United States Patent [19]

Betteridge

[11] Patent Number: 4,642,289

[45] Date of Patent: Feb. 10, 1987

[54] PROCESS FOR CELL DISRUPTION

[75] Inventor: Peter R. Betteridge, Sittingbourne, England

[73] Assignee: Shell Oil Company, Houston, Tex.

[21] Appl. No.: 642,915

[22] Filed: Aug. 21, 1984

[30] Foreign Application Priority Data

Aug. 26, 1983 [GB] United Kingdom ................. 8323058

[51] Int. Cl.$^4$ .......................... C12P 19/04; C12N 1/06; C12N 1/20
[52] U.S. Cl. .................................... 435/101; 435/253; 435/259; 435/267; 435/274; 435/317; 435/874
[58] Field of Search ...................... 435/101, 253, 172.3, 435/259, 874, 317, 267, 274; 935/72

[56] References Cited

U.S. PATENT DOCUMENTS 4,481,294 11/1984 Downs ................................ 435/267

FOREIGN PATENT DOCUMENTS 78556 5/1983 European Pat. Off. .

OTHER PUBLICATIONS

Datta et al., (1971), J. Bacteriol, vol. 108(3), pp. 1244–1249.
Boucher et al., (1977), J. Gen. Microbiol., vol. 98, pp. 253–263.

Primary Examiner—Charles F. Warren
Assistant Examiner—M. Moskowitz

[57] ABSTRACT

Process for disrupting cells of a polysaccharide-producing microorganism of the genus Pseudomonas, preferably Pseudomonas sp. NCIB 11592, which contain one or more RP4 and/or RP4::Mu$_{ts}$ plasmids.

Pseudomonas sp. NCIB 11592 containing one or more plasmids. Process for preparing polysaccharides by cultivating the latter. Process for displacing a fluid through a well and/or a permeable subsurface formation using the polysaccharides.

5 Claims, No Drawings

PROCESS FOR CELL DISRUPTION

BACKGROUND OF THE INVENTION

1. Field of the Invention

This invention relates to an improved process for disrupting cells, and in particular to a process for disrupting cells of a polysaccharide-producing microorganism of the genus Pseudomonas.

2. Description of the Prior Art

In microbiological processes it is often necessary in the later stages to disrupt the bacterial cells. Especially in the microbial production of polysaccharides for use as viscosifiers in enhanced oil recovery this is a major requirement. Cellular debris and non-viable bacteria have to be removed from the polysaccharide-containing solution before these solutions can be used in enhanced oil recovery operations, because it is the presence of these particulate solids in the polysaccharide solution which can present considerable difficulty in field application of the polymer flood when causing plugging of the rock face and injection water filters.

In European Patent Application No. 0078556, a process for cell disruption is described which comprises the contacting of an aqueous, cell-containing medium containing microorganisms, e.g. of the genus Pseudomonas, known to produce polysaccharides, with a protease enzyme, wherein the enzymic contact is preceded by contact with a surfactant.

Further research efforts on cell disruption have now resulted in the surprising finding that a remarkable improvement, especially in the efficiency of the surfactant treatment step, is achieved when the cells of microorganisms of the genus Pseudomonas contain one or more RP4 and/or RP4::$Mu_{ts}$ plasmids. For a description of these plasmids, reference is made to Datta, N. et al., *Journal of Bacteriology*, Vol. 108, pp 1244–1249 (1971), and Boucher, C., et al., *Journal of General Microbiology*, Vol. 98, pp 253–263. Although Pseudomonas cells comprising one or more of these plasmids appear to be more easily lysed by the surfactant than Pseudomonas cells not containing these plasmids, derivatives of other biopolymer-producing bacteria containing these plasmids showed no change in their sensitivity to the surfactant.

It might be possible that plasmid/transposon mutagenesis occurs in the Pseudomonas-DNA, which means that pieces of DNA from the plasmids integrate in Pseudomonas-DNA and in this way activate or inactivate certain genes which are responsible for rendering the Pseudomonas cells more sensitive to the surfactant.

Therefore, in this application the description "Pseudomonas cells containing one or more RP4 and/or RP4::$Mu_{ts}$ plasmids" not only encompasses Pseudomonas cells containing plasmids without the occurrence of transposon mutagenesis but also Pseudomonas cells in which plasmid transposon mutagenesis occurs or has occurred.

SUMMARY OF THE INVENTION

Accordingly, the present invention provides a process for disrupting cells of a polysaccharide-producing microorganism of the genus Pseudomonas with a non-ionic or anionic surfactant, comprising contacting the cells containing one or more RP4 and/or RP4::$Mu_{ts}$ plasmids with the surfactant and recovering a substantially cell-free polysaccharide.

The present process is particularly suitable for disrupting cells of the microorganism Pseudomonas sp. NCIB 11592 which is described in European Patent Application No. 0040445 and its corresponding copending U.S. application, Ser. No. 443,985, filed Nov. 23, 1982, now abandoned.

The surfactant used in the present process is preferably an anionic surfactant. A preferred one is an alkali metal alkyl sulfate, alkylbenzene sulfonate, sulfated alkanol ethoxylate or sulfated alkanol, in which the alkyl chain contains at least 8 carbon atoms.

Examples of suitable surfactants are sodium dodecyl sulfate (SDS), "Dobanol" 25-3S, sodium salt, a sulfated alkanolethoxylate. "Dobanol" 23-2S, sodium salt, a sulfated alkanol ethoxylate. "Teepol" HB67, sodium salt of $C_{9-13}$ primary alcohol sulfate. "Dobanic" acid 83, an alkylbenzene sulphonate and "Dobanic" acid JN, an alkylbenzene sulfonate.

The present invention further provides a process as hereinbefore described in which after the cells have been contacted with the surfactant they are contacted with an enzyme to degrade the bacterial cells. This enzyme may be alkaline, neutral or acid protease enzymes well known in the literature, but preferably an alkaline protease. The present process represents an improvement with regard to the earlier process of that nature as described in the European Patent Application No. 0078556 as was mentioned before and its corresponding U.S. Pat. No. 4,481,294.

Suitable alkaline proteases are "Alcalase", "Esperase", "Kitalase" and "Savinase", all being from bacterial origin. Good results are obtained with "Alcalase".

For most effective results the cell-containing medium should be contacted with the surfactant at a pH below about 6.0, preferably below about pH 4.5, while the subsequent contact with the enzyme should be at that pH at which the enzyme is most active; for alkaline proteases this pH is above about 6.0, suitably between about pH 7.0 and about pH 9.0. For both the surfactant and the enzyme treatment the temperature is suitably above room temperature but not high enough to degrade the enzyme or the polysaccharide, e.g. about 50°–60° C.

The process of the invention is of particular value in the degradation/solubilization of the cellular components in the broth obtained by fermentation of a nutrient medium of said Pseudomonas containing one or more RP4:$Mu_{ts}$ plasmids. The treatment by surfactant optionally followed by an enzyme according to the present invention enables such Pseudomonas cells to be disrupted and thereby solubilized. This makes it possible to produce a polysaccharide solution suitable for use in enhanced oil recovery by (a) cultivation of a suitable Pseudomonas in a nutrient medium; (b) contacting the resultant fermentation broth with an anionic surfactant optionally followed with an enzyme to degrade the bacterial cells; and (c) filtering the solution to remove any residual solid matter which could block the oil-bearing reservoir rock.

The present invention further provides a process for the incorporation into a microorganism of the genus Pseudomonas microorganism of one or more RP4 and/or RP4::$Mu_{ts}$ plasmids according to methods known in the art, e.g. as in the *Journal of General Microbiology*, 98, p 253–263 (1977). This is suitably achieved by transferring RP4 and/or RP4::$Mu_{ts}$ plasmids from a microorganism comprising one or more of these plasmids to Pseudomonas species. For instance, *E. coli* RP4 can be used as a source of RP4 plasmids. The present invention also provides Pseudomonas sp. NCIB 11592 which contain one or more RP4 and/or RP4::Mu$_{ts}$ plasmids.

Further, the present invention provides a process for the preparation of polysaccharides which comprises cultivating (fermenting) Pseudomonas sp. NCIB 11592 which contain one or more RP4 and/or RP4::Mu$_{ts}$ plasmids under aerobic conditions in an aqueous nutrient medium and recovering the polysaccharide from the polysaccharide-containing medium (broth). It is suitable to use process conditions which are the same or similar to those of the process for the production of a polysaccharide as described in European Patent Application No. 0040445. Still further, the present invention provides a process for displacing a fluid through a well and/or a permeable subsurface formation communicating with the well, by injecting into the well an aqueous solution which contains a viscosifier a polysaccharide as produced by the above process. The prime objective in applying the cell disruption process to polysaccharide broths destined for use in enhanced oil recovery is to prevent the cellular debris from causing plugging of the oil-bearing rock.

The present invention will be further described with reference to the following General Description of the Experimental Part and the Examples.

GENERAL DESCRIPTION OF THE EXPERIMENTAL PART

Bacteria were grown overnight at 30° C. on an orbital incubator (at 220 rpm) in dYT (g/l: Tryptone, 16; Yeast Extract, 10: NaCl, 5), then subcultured into 1 in 20 into fresh medium (50 ml in 250 ml Erlenmeyer flasks) and incubated for approximately 6 hours. Bacteria were harvested by centrifugation (3,000 g×15 min), and resuspended in fresh dYT. Cultures were incubated at 50° C., unless noted, for 30 min, split into 2 ml portions and SDS (sodium dodecyl sulfate), added to give final percentage shown. Samples were incubated for 30 min at room temperature on a rotating incubator.

Effect of lysis treatment was measured by absorbance at 600 nm compared with untreated controls. Results are expressed as percent absorbance remaining after treatment: 100%=no lysis.

EXAMPLE I

Table 1 shows the effect of culture age in case of lysis of the cells of Pseudomonas sp. NCIB 11592 containing RP4 plasmids and Pseudomonas sp.1 NCIB 11592 without RP4 plasmids by SDS (sodium dodecyl sulfate).

TABLE 1

| Age (hours) | Culture | SDS (sodium) dodecyl sulfate)/ percent absorbance remaining after treatment relative to a control | | |
|---|---|---|---|---|
| | | 0 | 0.075 | 0.1 |
| 22 | NCIB 11592 | 101 | 105 | 100 |
| | NCIB 11592/RP4 | 100 | 46 | 37 |
| 6 | NCIB 11592 | 100 | 91 | 83 |
| | NCIB 11592/RP4 | 103 | 11 | 7 |

All in dYT "means" g/l: Tryptone, 16; Yeast Extract, 10; NaCl, 5.
Modification: The overnight culture was incubated further = 22 hr culture.

EXAMPLE II

Table 2 shows the effect of pH change of lysis medium on lysis and the effect of applying or omitting the pretreatment at 50° C. (for 30 min) of cells of Pseudomonas sp. NCIB 11592 with and without RP4 plasmids.

TABLE 2

| Test | Pretreatment pH | at 50° C. | RP4 Plasmid | SDS (sodium dodecyl sulfate)/percent absorbance remaining after treatment relative to a control | | |
|---|---|---|---|---|---|---|
| | | | | 0 | 0.075% | 0.1% |
| 1 | 5 | — | — | 99 | 109 | 95 |
| 2 | 6 | — | — | 102 | 92 | 83 |
| 3 | 7 | — | — | 99 | 91 | 82 |
| 4 | 5 | — | + | 100 | 36 | 30 |
| 5 | 6 | — | + | 100 | 69 | 55 |
| 6 | 7 | — | + | 99 | 44 | 31 |
| 7 | 5 | + | — | 103 | 102 | 88 |
| 8 | 6 | + | — | 104 | 90 | 76 |
| 9 | 7 | + | — | 101 | 74 | 66 |
| 10 | 5 | + | + | 99 | 66 | 59 |
| 11 | 6 | + | + | 100 | 60 | 53 |
| 12 | 7 | + | + | 100 | 10 | 6 |

Tests 1-3 and 7-9 refer to Pseudomonas NCIB 11592.
Tests 4-6 and 10-12 refer to Pseudomonas NCIB 11592 comprising RP4 plasmid.

EXAMPLE III

Table 3 shows the results of an experiment of the lysis of Xanthomonas campestris NCIB 11854 with and without plasmids RP4 and Xanthomonas campestris NCIB 11808 by SDS (sodium dodecyl sulfate) and "Alcalase". The SDS (sodium dodecyl sulfate) results are for bacteria in dYT (g/l: Tryptone 16; Yeast Extract, 10; NaCl, 5) and for enzyme "Alcalase" lysis the bacteria were resuspended in 50 mM Tris-HCl buffer pH 8.0.

TABLE 3

| | NCIB 11854 | NCIB 11854/RP4 | NCIB 11808 |
|---|---|---|---|
| SDS (sodium dodecyl sulfate) % | | | |
| 0 | 100 | 100 | 100 |
| .005 | 78 | 75 | 73 |
| .0075 | 79 | 84 | 78 |
| .01 | 84 | 81 | 86 |
| .02 | 85 | 65 | 73 |
| .03 | 29 | 29 | 62 |
| .04 | 15 | 14 | 18 |
| .05 | 12 | 11 | 12 |
| .075 | 8 | 8 | 9 |
| Alcalase (μl) | | | |
| 0 | 100 | 100 | 100 |
| 4 | 18 | 22 | 18 |
| 7 | 19 | 21 | 19 |

EXAMPLE IV

Table 4 shows the results of an experiment on the lysis of Pseudomonas sp. NCIB 11592 with and without plasmids RP4 by SDS (sodium dodecyl sulfate) or "Alcalase". The SDS (sodium dodecyl sulfate) results are for bacteria in dYT (g/l: Tryptone 16; Yeast Extract, 10; NaCl, 5), and for enzyme ("Alcalase") lysis the bacteria were resuspended in 50 mM Tris-HCl buffer, pH 8.0.

TABLE 4

| | NCIB 11592 | NCIB 11592/ RP4 |
|---|---|---|
| SDS (sodium dodecyl sulfate) % | | |
| 0 | 100 | 100 |
| .01 | 110 | 116 |
| .02 | 126 | 111 |
| .04 | 119 | 50 |

TABLE 4-continued

| | NCIB 11592 | NCIB 11592/ RP4 |
|---|---|---|
| .06 | 110 | 26 |
| .08 | 103 | 18 |
| .1 | 98 | 12 |
| .125 | 94 | 10 |
| .15 | 87 | 9 |
| .175 | 82 | 8 |
| Alcalase (μl) | | |
| 0 | 100 | 100 |
| 5 | 96 | 94 |
| 12.5 | 95 | 96 |
| 15 | 95 | 96 |
| 17.5 | 96 | 96 |
| 20 | 96 | 97 |
| 22.5 | 96 | 97 |
| 25 | 96 | 97 |
| 30 | 99 | 96 |

What is claimed is:

1. A process for disrupting cells of polysaccharide-producing microorganism Pseudomonas sp. NCIB 11592 which contain one or more RP4 or RP4::Mu$_{ts}$ plasmids with an anionic surfactant which comprises contacting said cells with a surfactant for a time and under conditions sufficient to lyse said cells and recovering a substantially cell-free polysaccharide from said cell lysate.

2. A process according to the process of claim 1, in which the surfactant is an alkali metal alkyl sulfate, alkylbenzene sulfonate, sulfated alkanol ethoxylate or a sulfated alkanol, in each of which the alkyl chain contains at least eight carbon atoms.

3. A process according to the process of claim 1 in which after the cells have been contacted with the surfactant they are contacted with an alkaline protease.

4. A process according to claim 1 which further comprises cultivating said cells under aerobic conditions in an aqueous nutrient medium.

5. A process according to claim 4 in which after the cells have been contacted with the surfactant they are contacted with an alkaline protease.

* * * * *